United States Patent
Matsui et al.

(10) Patent No.: US 12,357,601 B2
(45) Date of Patent: Jul. 15, 2025

(54) COMPOSITION FOR INHIBITING GROWTH OF BACTERIUM HAVING MENAQUINONE SYNTHESIS PATHWAY THROUGH FUTALOSINE OR FUTALOSINE DERIVATIVE

(71) Applicant: NOSTER INC., Kyoto (JP)

(72) Inventors: Hidenori Matsui, Tokyo (JP); Marina Kawaguchi, Kyoto (JP)

(73) Assignee: NOSTER INC., Kyoto (JP)

( * ) Notice: Subject to any disclaimer, the term of this patent is extended or adjusted under 35 U.S.C. 154(b) by 0 days.

(21) Appl. No.: 17/732,057

(22) Filed: Apr. 28, 2022

(65) Prior Publication Data

US 2023/0285343 A1    Sep. 14, 2023

Related U.S. Application Data

(62) Division of application No. 16/494,661, filed as application No. PCT/JP2018/006804 on Feb. 23, 2018, now Pat. No. 11,337,947.

(30) Foreign Application Priority Data

Mar. 17, 2017    (JP) .................. 053056/2017

(51) Int. Cl.
  *A61K 31/201*    (2006.01)
  *C07K 14/205*    (2006.01)
  *A61K 38/00*    (2006.01)

(52) U.S. Cl.
  CPC .......... *A61K 31/201* (2013.01); *C07K 14/205* (2013.01); *A61K 38/00* (2013.01)

(58) Field of Classification Search
  CPC .................................................. A61K 31/201
  See application file for complete search history.

(56) References Cited

U.S. PATENT DOCUMENTS

| | | | |
|---|---|---|---|
| 2,852,521 | A | 9/1958 | Nichols |
| 2,852,522 | A | 9/1958 | Nichols |
| 2,894,964 | A | 7/1959 | Joseph et al. |
| 2009/0036533 | A1 | 2/2009 | Kim et al. |
| 2011/0064789 | A1 | 3/2011 | Touati |
| 2015/0342916 | A1 | 12/2015 | Ogawa et al. |
| 2016/0000739 | A1* | 1/2016 | Ogawa ............ A23K 20/158 514/560 |
| 2017/0000752 | A1* | 1/2017 | Ogawa ............ A61K 31/201 |

FOREIGN PATENT DOCUMENTS

| | | |
|---|---|---|
| CN | 104902887 A | 9/2015 |
| CN | 104994846 A | 10/2015 |
| JP | 2002085012 A | 3/2002 |
| JP | 2015-117220 A | 6/2015 |

OTHER PUBLICATIONS

Cover et al., Helicobacter pylori in health and disease, Gastroenterology. May 2009; 136(6): 1863-1873.*
Yamamoto et al., Narrow-spectrum inhibitors targeting an alternative menaquinone biosynthetic pathway of Helicobacter pylon, J. Infect. Chemother, 22(2016) 587-592.
European Search Report, EP 18768210, dated Dec. 2, 2020.
Hiratsuka et al., An Alternative Menaquinone Biosynthetic Pathway Operating in Microorganisms, Science, 321(5896):1670-1673 (2008).
International Search Report Corresponding International Application No. PCT/JP2018/006804, dated Apr. 24, 2018, 18 pages (9 pages of English Translation and 9 pages of Original Document).
Matsui et al., Mouse Models for Assessing the Protective Efficacy of Lactobacillus Gasseri SBT2055 Against Helicobacter Suis Infection Associated With the Development of Gastric Mucosa-Associated Lymphoid Tissue Lymphoma, Helicobacter, 20 (4):291-298 (2015).
Matsui et al., Protective efficacy of a hydroxy fatty acid against gastric Helicobacter infections, Helicobacter, 22(6): 312430 (2017).
Santos et al., Therapeutic Supplementation of Caprylic Acid in Feed Reduces Campylobacter jejuni Colonization in Broiler Chicks, Appl. Environ., Microbiol. 74(14):4564-4566 (2008).
Tanaka et al., Branched Fatty Acids Inhibit the Biosynthesis of Menaquinone in Helicobacter Pylori, J. Antibiot., 64:151-153 (2011).
Thompson et al., Inhibitory Effect of Polyunsaturated Fatty Acids on the Growth of Helicobacter pylori: A Possible Explanation of the Effect of Diet on Peptic Ulceration, Gut, 35 (11):1557-1561 (1994).
CN App. No. 2018800189166; Search Report mailed Jun. 15, 2022.
Andrea Baccarelli et al., "Mannose-binding lectin-2 genetic variation and stomach cancer risk"; Int. J. Cancer, vol. 119, 1970-1975 (2006).
Chey et al., ACG clinical guideline: treatment of Helicobacter pylori infection, Am. J. Gastroenterol., 112: 212-238, (Feb. 2017).
Kuwana, Helicobacter pylori-associated immune thrombocytopenia: clinical features and pathogenic mechanisms, World J. Gastroenterol., 20(3): 714-723, (Jan. 2014).
Camci et al., Association between Parkinson's disease and Helicobacter pylori, J. Clin. Neurol., 12(2): 147-150, (2016).
Fukuda et al., Effect of Helicobacter pylori eradication in the treatment of Japanese patients with chronic idiopathic urticaria, J. Gastroeneterol., 39: 827-830, (2004).

(Continued)

*Primary Examiner* — Svetlana M Ivanova
(74) *Attorney, Agent, or Firm* — MARSHALL, GERSTEIN & BORUN LLP

(57) ABSTRACT

The present invention provides a composition for inhibiting proliferation of a bacterium provided with a menaquinone synthesis route via futalosine or a futalosine derivative, which contains a fatty acid having 18 carbon atoms and a hydroxyl group at the 10-position as an active ingredient. Furthermore, the present invention provides a composition for preventing or treating a disease caused by a bacterium provided with a menaquinone synthesis route via futalosine or a futalosine derivative.

9 Claims, 12 Drawing Sheets

Specification includes a Sequence Listing.

(56) References Cited

OTHER PUBLICATIONS

Epps et al., Foodborne campylobacter: infections, metabolism, pathogenesis and resevoirs, Int. J. Environ. Res. Public Health, 10: 6292-6304, (2013).

Poropatich et al., Quantifying the association between campylobacter infection and Guillain-Barre syndrome: a systematic review, J. Health Popul. Nutr., 28(6): 545-552, (Dec. 2010).

* cited by examiner

COMPOSITION FOR INHIBITING GROWTH OF BACTERIUM HAVING MENAQUINONE SYNTHESIS PATHWAY THROUGH FUTALOSINE OR FUTALOSINE DERIVATIVE

CROSS REFERENCE TO RELATED APPLICATIONS

This application is a divisional of the U.S. patent application Ser. No. 16/494,661 filed Sep. 16, 2019, which is a U.S. National Stage of International Application No. PCT/JP2018/006804, filed Feb. 23, 2018, which claims the benefit of Japanese Patent Application No. 2017-053056, filed Mar. 17, 2017, the entire contents of each of which are fully incorporated herein by reference.

INCORPORATION BY REFERENCE OF MATERIAL SUBMITTED ELECTRONICALLY

A Sequence Listing, which is a part of the present disclosure, is submitted concurrently with the specification as a text file. The name of the text file containing the Sequence Listing is "54774_Seqlisting.txt." The Sequence Listing was created on Sep. 16, 2019, and is 2,177 bytes in size. The subject matter of the Sequence Listing is incorporated herein in its entirety by reference.

TECHNICAL FIELD

The present invention relates to a composition containing a fatty acid having 18 carbon atoms and a hydroxyl group at the 10-position as an active ingredient for suppressing proliferation of a bacterium provided with a menaquinone synthesis route via futalosine or a futalosine derivative (preferably, *Helicobacter* bacterium or *Campylobacter* bacterium). Furthermore, the present invention relates to a composition for preventing or treating a disease caused by *Helicobacter* bacterium or a composition for preventing or treating a disease caused by *Campylobacter* bacterium. In addition, the present invention also relates to the composition as a food, a pharmaceutical product, a feed or the like.

BACKGROUND ART

At present, about 50% of the population is considered to have *Helicobacter* bacterium in the gastrointestinal tract. *Helicobacter* bacterium carriers may not have subjective symptoms but it is known that gastritis, stomach pain or stomach cancer is developed. Since the route of infection with *Helicobacter* bacterium is oral or fecal route, the infection rate of *Helicobacter* bacteria is high in the developing countries where hygiene state is poor.

When infected with *Helicobacter pylori*, which is one kind of *Helicobacter* bacteria, the infection is detected by a urease test (13C-UREA BREATH TEST), and is treated by eradication. As the eradication method, a three agent combination therapy using a proton pump inhibitor that suppresses secretion of gastric acid and antibiotics (penicillin-based and macrolide-based) has been established. The eradication rate is said to be about 90% and *Helicobacter pylori* that could not be eradicated may proliferate again. In addition, this eradication method has been reported to cause side effects such as diarrhea, gustation disorder, allergy, emergence of multiple drug resistant bacteria and the like. The side effects are considered to be mainly caused by changes in the intestinal bacterial flora due to the administration of a large amount of antibiotics having broad spectrum.

Among the *Helicobacter* bacteria that infect the human stomach, *Helicobacter suis* is difficult to diagnose since it is often negative for the urease test even if infection is present and is a hardly culturable bacterium. Thus, an eradication method has not been established. Furthermore, about 60% of the patients who developed gastric MALT lymphoma, which is one type of stomach cancer, show negative *Helicobacter pylori* test results but are known to be infected with bacteria such as *Helicobacter suis* and the like included in *Helicobacter heilmannii* sensu lato.

Poultry infected with *Campylobacter* bacteria is a major cause of food poisoning in human. In particular, the carrying rate of the distributing chicken is said to be high. While the possibility of contamination with *Campylobacter* bacteria in poultry houses and chicken processing plants is mentioned, the exact source of contamination is unknown even now. Fever and gastrointestinal inflammation are the main symptoms of human *Campylobacter* infection, and the complications thereof include Guillain-Barre syndrome which is a neurological disorder.

As a probiotic bacterium that inhibits proliferation of *Helicobacter* bacteria, *Lactobacillus gasseri* has been reported (patent document 1, non-patent document 1). It is well known that menaquinone (vitamin K2) is an essential component of the electron transport system of bacteria. It is suggested that *Helicobacter* bacteria and *Campylobacter* bacteria are provided with a menaquinone synthesis route via futalosine or a futalosine derivative (non-patent document 2), and this synthesis route is different from the menaquinone synthesis route that *lactobacillus, Escherichia coli* and the like have. It has heretofore been reported that straight chain unsaturated fatty acid (patent document 2, non-patent document 3, non-patent document 4) and branched saturated fatty acid (non-patent document 5), which are considered to target menaquinone synthesis route via futalosine or a futalosine derivative, have an effect of inhibiting proliferation of *Helicobacter pylori*. Furthermore, foods and drinks for eradicating *Helicobacter pylori* containing free hydroxy fatty acid as an active ingredient have been reported. (patent document 3). In addition, as a compound inhibiting proliferation of *Campylobacter* bacterium, caprylic acid, which is a middle chain fatty acid, is known (non-patent document 6).

As mentioned above, since the synthesis route of menaquinone varies depending on the bacterium, a compound capable of more strongly blocking only the menaquinone synthesis route possessed by pathogenic microorganisms including *Helicobacter* bacterium and *Campylobacter* bacterium can inhibit proliferation of pathogenic microorganisms without breaking intestinal bacterial flora. Therefore, a compound capable of more efficiently inhibiting menaquinone synthesis route via futalosine or a futalosine derivative has been demanded.

DOCUMENT LIST

Patent Documents patent document 1: JP-A-2015-117220
patent document 2: US2011/0064789A1
patent document 3: JP-A-2002-85012

Non-Patent Document non-patent document 1: H. Matsui, et al., Mouse Models for Assessing the Protective Efficacy of *Lactobacillus* gasseri SBT2055 against *Helicobacter suis* Infection Associated with the Development of Gastric Mucosa-Associated Lymphoid Tissue Lymphoma, *Helicobacter*, 2015; 20: 291-298 non-patent document 2: T. Hiratsuka, et al., An Alternative Menaquinone Biosynthetic Pathway Operating in Microorganisms, Science, 2008 Sep. 19; 321(5896): 1670-3 non-patent document 3: T. Yamamoto, et al., Narrow-spectrum inhibitors targeting an alternative menaquinone biosynthetic pathway of *Helicobacter pylori*, J. Infect. Chemother., 2016 September; 22(9):587-92 non-patent document 4: L. Thompson, et al., Inhibitory effect of polyunsaturated fatty acids on the growth of *Helicobacter pylori*: a possible explanation of the effect of diet on peptic ulceration, Gut, 1994; 35: 1557-1561 non-patent document 5: R. Tanaka, et al., Branched fatty acids inhibit the biosynthesis of menaquinone in *Helicobacter pylori*, J. Antibiot., 2011; 64: 151-153 non-patent document 6: F. Solis de los Santos, et al., Therapeutic Supplementation of Caprylic Acid in Feed Reduces *Campylobacter jejuni* Colonization in Broiler Chicks, Appl. Environ. Microbiol., 2008 July; 74 (14): 4564-6

SUMMARY OF THE INVENTION

Problems to be Solved by the Invention

It is an object of the present invention to find a compound that inhibits menaquinone synthesis route via futalosine or a futalosine derivative more efficiently from known compounds that inhibit the route, and provide a composition for inhibiting of a bacterium provided with menaquinone synthesis route via futalosine or a futalosine derivative, which contains the compound as an active ingredient, and further, a composition for preventing or treating a disease caused by a bacterium provided with a menaquinone synthesis route via futalosine or a futalosine derivative.

Means of Solving the Problems

In view of the above-mentioned problems, the present inventors have conducted intensive studies and found that a fatty acid having 18 carbon atoms and a hydroxyl group at the 10-position has an inhibitory action on the proliferation of *Helicobacter pylori* and *Helicobacter suis*, a suppressive action on an increase in the number of Ki-67 positive cells, a suppressive action on an increase in the CD19 expression level and CD20 expression level, and a suppressive action on the onset of pathology of gastric MALT lymphoma, which are physiological functions not conventionally known. Also, the present inventors have found that a fatty acid having 18 carbon atoms and a hydroxyl group at the 10-position has an inhibitory action on proliferation of *Campylobacter jejuni* and *Campylobacter coli*.

Based on the above findings, the present invention has been completed.

That is, the present invention is as follows.

[1] A composition for inhibiting proliferation of a bacterium provided with a menaquinone synthesis route via futalosine or a futalosine derivative, comprising a fatty acid having 18 carbon atoms and a hydroxyl group at the 10-position.

[2] The composition of [1] wherein the fatty acid has a cis double bond at at least the 12-position.

[3] The composition of [2] wherein the fatty acid is at least one selected from the group consisting of 10-hydroxy-cis-12-octadecenoic acid, 10-hydroxy-cis-12,cis-15-octadecadienoic acid and 10-hydroxy-cis-6,cis-12-octadecadienoic acid.

[4] The composition of [3] wherein the fatty acid is 10-hydroxy-cis-12-octadecenoic acid.

[5] The composition of any one of [1] to [4] wherein the bacterium is *Helicobacter* bacterium.

[6] The composition of [5] wherein the *Helicobacter* bacterium is selected from the group consisting of *Helicobacter pylori* and *Helicobacter suis*.

[7] The composition of [5] or [6] for use in preventing or treating a disease selected from the group consisting of acute gastritis, chronic gastritis, nodular gastritis, gastric ulcer, duodenal ulcer, stomach cancer, stomach MALT lymphoma, diffuse large B-cell lymphoma, idiopathic thrombocytopenic purpura, childhood hypoferric anemia, chronic urticaria and Parkinson's disease.

[8] The composition of any one of [1] to [4] wherein the bacterium is *Campylobacter* bacterium.

[9] The composition of [8] wherein the *Campylobacter* bacterium is selected from the group consisting of *Campylobacter jejuni* and *Campylobacter coli*.

[10] The composition of [8] or [9] for use in preventing or treating *Campylobacter* food poisoning or Guillain-Barre syndrome.

[11] The composition of any one of [1] to [10] which is a food or a food additive.

[12] The composition of any one of [1] to [10] which is a pharmaceutical product.

[13] The composition of any one of [1] to [10] which is a feed or a feed additive.

[14] A method for inhibiting proliferation of a bacterium provided with a menaquinone synthesis route via futalosine or a futalosine derivative, comprising administering a fatty acid having 18 carbon atoms and a hydroxyl group at the 10-position to a subject.

[15] A method for preventing or treating a disease selected from the group consisting of acute gastritis, chronic gastritis, nodular gastritis, gastric ulcer, duodenal ulcer, stomach cancer, stomach MALT lymphoma, diffuse large B-cell lymphoma, idiopathic thrombocytopenic purpura, childhood hypoferric anemia, chronic urticaria and Parkinson's disease, comprising administering a fatty acid having 18 carbon atoms and a hydroxyl group at the 10-position to a subject.

[16] A method for preventing or treating *Campylobacter* food poisoning or Guillain-Barre syndrome, comprising administering a fatty acid having 18 carbon atoms and a hydroxyl group at the 10-position to a subject.

[17] A fatty acid having 18 carbon atoms and a hydroxyl group at the 10-position for use in preventing or treating a disease selected from the group consisting of acute gastritis, chronic gastritis, nodular gastritis, gastric ulcer, duodenal ulcer, stomach cancer, stomach MALT lymphoma, diffuse large B-cell lymphoma, idiopathic thrombocytopenic purpura, childhood hypoferric anemia, chronic urticaria and Parkinson's disease.

[18] A fatty acid having 18 carbon atoms and a hydroxyl group at the 10-position for use in preventing or treating *Campylobacter* food poisoning or Guillain-Barre syndrome.

[19] Use of a fatty acid having 18 carbon atoms and a hydroxyl group at the 10-position in the production of a proliferation inhibitor of a bacterium provided with a menaquinone synthesis route via futalosine or a futalosine derivative.

[20] Use of a fatty acid having 18 carbon atoms and a hydroxyl group at the 10-position in the production of an agent for preventing or treating a disease selected from the group consisting of acute gastritis, chronic gastritis, nodular gastritis, gastric ulcer, duodenal ulcer, stomach cancer, stomach MALT lymphoma, diffuse large B-cell lymphoma, idiopathic thrombocytopenic purpura, childhood hypoferric anemia, chronic urticaria and Parkinson's disease.

[21] Use of a fatty acid having 18 carbon atoms and a hydroxyl group at the 10-position in the production of an agent for preventing or treating *Campylobacter* food poisoning or Guillain-Barre syndrome.

Effect of the Invention

The present invention provides a composition containing a fatty acid having 18 carbon atoms and a hydroxyl group at the 10-position as an active ingredient for suppressing proliferation of a bacterium provided with a menaquinone synthesis route via futalosine or a futalosine derivative, and further, a composition for preventing or treating a disease caused by a bacterium provided with a menaquinone synthesis route via futalosine or a futalosine derivative. The compositions can be used in various fields such as pharmaceutical product, food, feed and the like, and thus the present invention is industrially extremely useful.

BRIEF DESCRIPTION OF THE DRAWINGS

FIG. 1-2 shows a proliferation suppressive effect (in vitro) of HYA on *Helicobacter pylori* TN2GF4 strain.

FIG. 1-3 shows a proliferation suppressive effect (in vitro) of HYA on *Helicobacter pylori* ATCC43579 strain.

FIG. 1-4 shows a proliferation suppressive effect (in vitro) of HYA on *Helicobacter pylori* NCTC11637 strain.

FIG. 1-5 shows a proliferation suppressive effect (in vitro) of HYA on *Helicobacter pylori* TY281 strain.

FIG. 1-6 shows a proliferation suppressive effect (in vitro) of HYA on *Helicobacter pylori* TY1345 strain.

FIG. 2-1 shows a proliferation suppressive effect (in vitro) of low concentration HYA on *Helicobacter pylori* SS1 strain.

FIG. 2-2 shows a proliferation suppressive effect (in vitro) of low concentration HYA on *Helicobacter pylori* TN2GF4 strain.

FIG. 2-3 shows a proliferation suppressive effect (in vitro) of low concentration HYA on *Helicobacter pylori* TK1029 strain.

FIG. 2-4 shows a proliferation suppressive effect (in vitro) of low concentration HYA on *Helicobacter pylori* RC-1 strain.

FIG. 3-1 shows a proliferation suppressive effect (in vivo) of fatty acid on *Helicobacter pylori* SS1 strain.

FIG. 3-2 shows a proliferation suppressive effect (in vivo) of fatty acid on *Helicobacter pylori* TN2GF4 strain.

FIG. 4-1 shows a proliferation suppressive effect (in vivo) of HYA on *Helicobacter pylori* SS1 strain.

FIG. 4-2 shows a proliferation suppressive effect (in vivo) of HYA on *Helicobacter pylori* TN2GF4 strain.

FIG. 4-3 shows a proliferation suppressive effect (in vivo) of HYA on *Helicobacter suis* TKY strain or SNTW101 strain.

FIG. 5-1 shows a proliferation suppressive effect (in vivo) of HYA on *Helicobacter suis* TKY strain.

FIG. 5-2 shows a suppressive effect (in vivo) of HYA on an increase in the number of Ki-67 positive cells in a stomach tissue of *Helicobacter suis* TKY strain-infected mouse.

FIG. 5-3 shows a suppressive effect (in vivo) of HYA on an increase in CD20 expression in a stomach tissue of *Helicobacter suis* TKY strain-infected mouse.

FIG. 5-4 shows a suppressive effect (in vivo) of HYA on an increase in CD19 expression in a stomach tissue of *Helicobacter suis* TKY strain-infected mouse.

FIG. 6-1 shows a proliferation suppressive effect (in vitro) of HYA on *Campylobacter jejuni* ATCC33560 strain.

FIG. 6-2 shows a proliferation suppressive effect (in vitro) of HYA on *Campylobacter coli* ATCC33559 strain.

FIG. 6-3 shows a proliferation suppressive effect (in vitro) of HYA on *Campylobacter jejuni* ATCC33560 strain.

FIG. 6-4 shows a proliferation suppressive effect (in vitro) of HYA on *Campylobacter coli* ATCC33559 strain.

DESCRIPTION OF EMBODIMENTS

Figure 1:
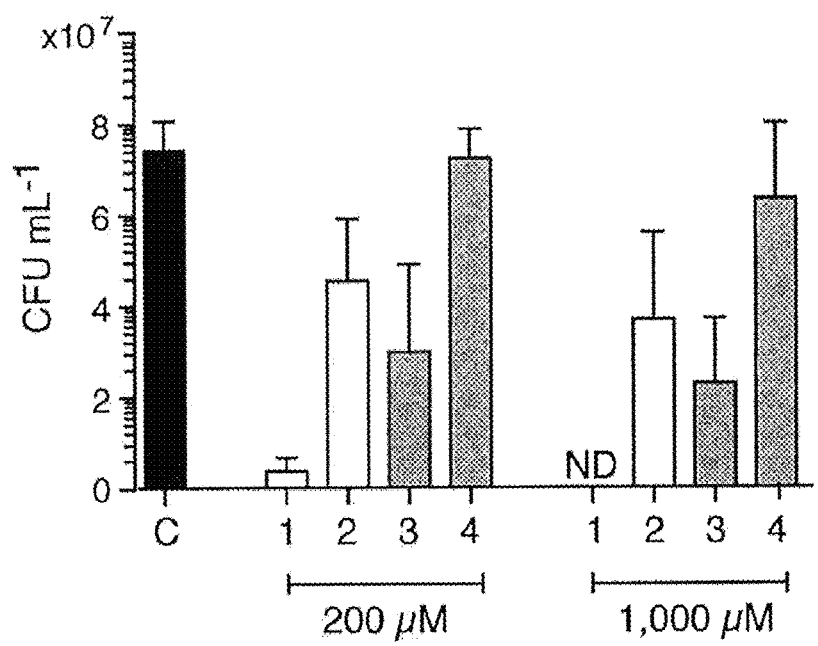
FIG. 1-1 shows a proliferation suppressive effect (in vitro) of HYA on *Helicobacter pylori* SS1 strain.

The present invention provides a composition for inhibiting proliferation of a bacterium provided with a menaquinone synthesis route via futalosine or a futalosine derivative, which contains a fatty acid having 18 carbon atoms and a hydroxyl group at the 10-position (hereinafter to be also referred to as the composition of the present invention).

The composition of the present invention contains a fatty acid having 18 carbon atoms and a hydroxyl group at the 10-position (hereinafter to be also referred to as the hydroxylated fatty acid in the present invention). The hydroxylated fatty acid in the present invention may be a saturated fatty acid or an unsaturated fatty acid. When it is an unsaturated fatty acid, an unsaturated fatty acid having at least one double bond selected from the group consisting of a cis double bond at the 6-position, a cis double bond at the 12-position, a cis double bond at the 15-position and a trans double bond at the 11-position is preferable, an unsaturated fatty acid having a cis double bond at at least the 12-position is more preferable.

More specifically, examples of the hydroxylated fatty acid in the present invention include 10-hydroxy-cis-12-octadecenoic acid (hereinafter to be also referred to as HYA), 10-hydroxy-cis-12,cis-15-octadecadienoic acid (hereinafter to be also referred to as αHYA), 10-hydroxy-cis-6,cis-12-octadecadienoic acid (hereinafter to be also referred to as γHYA), 10-hydroxy-cis-6,cis-12,cis-15-octadecatrienoic acid (hereinafter to be also referred to as sHYA), 10,12-dihydroxyoctadecanoic acid (hereinafter to be also referred to as rHYA), 10-hydroxy-trans-11-octadecenoic acid (hereinafter to be also referred to as HYC), 10-hydroxy-trans-11,cis-15-octadecadienoic acid (hereinafter to be also referred to as αHYC), 10-hydroxy-cis-6,trans-11-octadecadienoic acid (hereinafter to be also referred to as γHYC), 10-hydroxy-cis-6,trans-11,cis-15-octadecatrienoic acid (hereinafter to be also referred to as sHYC) and the like. It is preferably 10-hydroxy-cis-12-octadecenoic acid, 10-hydroxy-cis-12,cis-15-octadecadienoic acid or 10-hydroxy-cis-6,cis-12-octadecadienoic acid, further preferably 10-hydroxy-cis-12-octadecenoic acid.

The hydroxylated fatty acid in the present invention can be prepared by a known means and, for example, a production method is also described in WO 2013/168310. In addition, 10-hydroxy-cis-12-octadecenoic acid can be prepared by reference to Biochemical and Biophysical Research Communications, 416(2011), p. 188-193, and the like.

The hydroxylated fatty acid in the present invention has a proliferation inhibitory effect on a bacterium provided with a menaquinone synthesis route via futalosine or a futalosine derivative (hereinafter to be also referred to as futalosine synthesis bacterium). In the present invention, the futalosine synthesis bacterium is a bacterium provided with, in a metabolism pathway for biosynthesizing menaquinone, a metabolism pathway for biosynthesizing menaquinone from chorismic acid via futalosine or a futalosine derivative (hereinafter to be also referred to as futalosine pathway). As used herein, the futalosine derivative is, for example, aminodeoxyfutalosine, dehypoxanthinyl futalosine, cyclic dehypoxanthine futalosine or 1,4-dihydroxy-6-naphtoic acid. In the futalosine pathway, futalosine is synthesized from chorismic acid and inosine. Aminodeoxyfutalosine is synthesized from chorismic acid and adenosine. Futalosine or aminodeoxyfutalosine is metabolized into dehypoxanthinyl futalosine, dehypoxanthinyl futalosine is metabolized into cyclic dehypoxanthine futalosine, cyclic dehypoxanthine futalosine is metabolized into 1,4-dihydroxy-6-naphtoic acid, and finally, 1,4-dihydroxy-6-naphthoic acid is metabolized into menaquinone.

Menaquinone is an essential component in the electron transport system of bacteria, and two kinds of routes are known as synthesis routes in the bacteria. One is a route for synthesizing menaquinone from chorismic acid via succinylbenzoic acid (hereinafter to be also referred to as succinylbenzoic acid route), and it is provided in *Escherichia coli, lactobacillus*, bifidobacteria, *Enterococcus, Salmonella, Shigella, Listeria, Yersinia, Bacillus subtilis* and the like. The other is a futalosine pathway clarified by genetic analysis in recent years. As a bacterium having the both pathways of succinylbenzoic acid pathway and futalosine pathway, *Stackebrandtia nassauensis* DSM 44728 which is one species of actinomycetes is known to date. Except this bacterium, a bacterium provided with a metabolism pathway for biosynthesizing menaquinone is only provided with any one route of the above-mentioned routes. Therefore, the hydroxylated fatty acid in the present invention capable of inhibiting the futalosine pathway can specifically inhibit proliferation of futalosine synthesis bacterium. In the present invention, the futalosine synthesis bacterium is not particularly limited as long as it is provided with a futalosine pathway, and a bacterium not provided with a succinylbenzoic acid pathway is preferable. Examples of the futalosine synthesis bacterium include *Helicobacter* bacterium, *Campylobacter* bacterium, *Chlamydia* bacterium, *Thermus* bacterium, *Wolinella* bacterium, *Streptomyces* bacterium, *Acidothermus* bacterium, *Kitasatospora* bacterium, *Bacillus* bacterium and the like. In the present invention, examples of the *Helicobacter* bacterium include *Helicobacter pylori, Helicobacter heilmannii* sensu lato (including *Helicobacter suis, Helicobacter felis, Helicobacter salomonis, Helicobacter bizzozeronii, Helicobacter baculiformis, Helicobacter cynogastricus, Helicobacter heilmannii* sensu stricto), *Helicobacter anseris, Helicobacter acinonychis, Helicobacter bilis, Helicobacter brantae, Helicobacter canadensis, Helicobacter canis, Helicobacter cholecystus, Helicobacter cinaedi, Helicobacter hepaticus, Helicobacter muridarum, Helicobacter mustelae, Helicobacter pametensis, Helicobacter rodentium, Helicobacter trogontum* and the like, preferably, *Helicobacter pylori* and *Helicobacter suis*. In the present invention, examples of the *Campylobacter* bacterium include *Campylobacter coli, Campylobacter concisus, Campylobacter fetus, Campylobacter jejuni, Campylobacter sputorum, Campylobacter mucosalis, Campylobacter* rectus and the like, preferably, *Campylobacter jejuni* and *Campylobacter coli*. In the present invention, examples of the *Chlamydia* bacterium include *Chlamydia muridarum, Chlamydia suis, Chlamydia trachomatis* and the like. In the present invention, examples of the *Thermus* bacterium include *Thermus antranikianii, Thermus aquaticus, Thermus igniterrae, Thermus thermophilus* and the like. In the present invention, examples of the *Wolinella* bacterium include *Wolinella curva, Wolinella succinogenes, Wolinella recta* and the like. In the present invention, examples of the *Streptomyces* bacterium include *Streptomyces avermitilis, Streptomyces coelicolor, Streptomyces scabies, Streptomyces lividans* and the like. In the present invention, examples of the *Acidothermus* bacterium include *Acidothermus cellulolyticus* and the like. In the present invention, examples of the *Kitasatospora* bacterium include *Kitasatospora setae* and the like. In the present invention, examples of the *Bacillus* bacterium include *Bacillus cereus, Bacillus subtilis, Bacillus thuringiensis* and the like.

The hydroxylated fatty acid in the present invention can inhibit proliferation of futalosine synthesis bacterium, and thus can be used, when the futalosine synthesis bacterium is a bacterium that infects human or animals other than human and cause a disease (hereinafter to be also referred to as pathogenic futalosine synthesis bacterium), for the prophylaxis or treatment of the disease. Examples of the pathogenic futalosine synthesis bacterium include *Helicobacter* bacterium, *Campylobacter* bacterium, *Chlamydia* bacterium, *Wolinella* bacterium, *Bacillus* bacterium and the like. When the pathogenic futalosine synthesis bacterium is *Helicobacter* bacterium, examples of the disease that can be prevented or treated by the composition of the present invention include gastric diseases such as acute gastritis, chronic gastritis, nodular gastritis, gastric ulcer, duodenal ulcer, stomach cancer, gastric MALT lymphoma and the like, non-gastric diseases such as diffuse large B-cell lymphoma, idiopathic thrombocytopenic purpura, childhood hypoferric anemia, chronic urticaria and the like, Parkinson's disease and the like, preferably, gastric diseases such as acute gastritis, chronic gastritis, nodular gastritis, gastric ulcer, duodenal ulcer, stomach cancer, gastric MALT lymphoma and the like. When the pathogenic futalosine synthesis bacterium is *Campylobacter* bacterium, examples of the disease that can be prevented or treated by the composition of the present invention include *Campylobacter* food poisoning, Guillain-Barre syndrome and the like. When the pathogenic futalosine synthesis bacterium is *Chlamydia* bacterium, examples of the disease that can be prevented or treated by the composition of the present invention include *Chlamydia* infections, trachoma, pneumonia, parrot disease and the like. When the pathogenic futalosine synthesis bacterium is *Wolinella* bacterium, examples of the disease that can be prevented or treated by the composition of the present invention include periodontitis and the like. When the pathogenic futalosine synthesis bacterium is *Bacillus* bacterium, examples of the disease that can be prevented or treated by the composition of the present invention include food poisoning, bacteremia, pneumonia, endocarditis, ocular infections, opportunistic infection and the like.

The composition of the present invention can be used as, for example, pharmaceutical product, food, feed and the like, or by blending with them.

When the composition of the present invention is used as a pharmaceutical product, the dosage form of the pharmaceutical product includes dispersion, granule, pill, soft capsule, hard capsule, tablet, chewable tablet, quick-disintegrating tablet, syrup, liquid, suspension, suppository, ointment, cream, gel, adhesive, inhalant, injection and the like. A preparation thereof is prepared according to a conventional method.

Examples of the additives that can be used for forming preparations include animal and plant oils such as soybean oil, safflower oil, olive oil, germ oil, sunflower oil, beef tallow, sardine oil and the like, polyvalent alcohols such as polyethylene glycol, propylene glycol, glycerol, sorbitol and the like, surfactants such as sorbitan fatty acid ester, sucrose fatty acid ester, glycerin fatty acid ester, polyglycerol fatty acid ester and the like, excipients such as purified water, lactose, starch, crystalline cellulose, D-mannitol, lecithin, gum arabic, sorbitol solution, carbohydrate solution and the like, sweetener, colorant, pH adjuster, flavor and the like. A liquid preparation may be dissolved or suspended in water or other suitable medium when in use. Also, tablet and granules may be coated by a well-known method.

For administration in the form of an injection, intravenous, intraperitoneal, intramuscular, subcutaneous, transdermal, intraarticular, intrasynovial, intrathecal, intraperiosteum, sublingual, oral administrations and the like are preferable, and intravenous administration or intraperitoneal administration is particularly preferable. The intravenous administration may be any of drip administration and bolus administration.

When the composition of the present invention is used as a food or food additive, the food of the present invention is not particularly limited as long as it permits oral ingestion, such as solution, suspension, powder, solid formed article and the like. Specific examples include supplements (dispersion, granule, soft capsule, hard capsule, tablet, chewable tablet, quick-disintegrating tablet, syrup, liquid etc.), drinks (carbonic acid drinks, lactic acid drinks, sport drinks, fruit juice drinks, vegetable drinks, soymilk drinks, coffee drinks, tea drinks, powder drinks, concentrated drinks, nutrition drinks, alcohol drinks etc.), confectionery (gummy, jelly, gum, chocolate, cookie, candy, caramel, Japanese confectionery, snack etc.), instant food (instant noodles, retort food, can, microwavable foods, instant soup, miso soups, freeze-dried food etc.), oil, fats and oils food (mayonnaise, dressing, butter, cream, margarine etc.), wheat powder products (bread, pasta, noodle, cake mix, bread crumb etc.), seasoning (sauce, tomato processing seasoning, flavor seasoning, cooking mixture, soup etc.), processed meat products (meat ham, sausage and the like).

The above-mentioned foods can contain, where necessary, various nutrients, various vitamins (vitamin A, vitamin B1, vitamin B2, vitamin B6, vitamin C, vitamin D, vitamin E, vitamin K etc.), various minerals (magnesium, zinc, iron, sodium, potassium, selenium etc.), dietary fiber, dispersing agent, stabilizer such as emulsifier and the like, sweetener, flavor components (citric acid, malic acid etc.), flavor, royal jelly, propolis, *Agaricus* and the like.

When the composition of the present invention is used as a feed or feed additive, the feed of the present invention is, for example, pet food, stock raising or aquaculture feed additive and the like.

As the subject to be administered with or that ingests the composition of the present invention, human and animals other than human (e.g., dog, cat, mouse, rat, hamster, guinea pig, rabbit, swine, bovine, chicken, parakeet, hill myna, goat, horse, sheep, monkey etc.) can be mentioned.

While the dose or ingestion amount of the composition of the present invention varies depending on the subject of administration or ingestion, target disease, symptom, administration or ingestion route and the like, for example, a daily dose or ingestion amount of the fatty acid contained in the composition of the present invention is generally 0.02-100 mg/kg body weight, preferably 0.2-50 mg/kg body weight, more preferably 0.5-20 mg/kg body weight, which can be administered or ingested orally or parenterally. Plural divided portions may be administered or ingested per day. The dose may be increased or decreased according to the symptom.

The present invention is explained in more detail in the following by referring to Examples. The Examples are mere exemplifications of the present invention and do not limit the scope of the present invention in any manner.

EXAMPLES

Strain

The strains used in this Example are as follows. *Helicobacter pylori* SS1 strain is an experimental strain isolated from a patient with a stomach disease and adapted to infect mice. *Helicobacter pylori* TN2GF4 strain, NCTC11637 strain, ATCC43579 strain, TK1029 strain, TY281 strain and TY1345 strain are isolated from gastric biopsy specimens of patients with stomach diseases. *Helicobacter pylori* RC-1 strain is isolated from a gastric biopsy specimen of a patient with a stomach disease and is clarithromycin resistant. *Helicobacter suis* TKY strain is isolated from *Macaca fascicularis*. *Helicobacter suis* SNTW101 strain is isolated from a patient who developed nodular gastritis. *Campylobacter jejuni* ATCC33560 strain is a standard strain of *Campylobacter jejuni* isolated from bovine feces. *Campylobacter coli* ATCC33559 strain is a standard strain of *Campylobacter coli* isolated from swine feces.

Manufacture or Preparation of Fatty Acids

The fatty acid having 18 carbon atoms and a hydroxyl group or a carbonyl group at the 10-position (10-hydroxyoctadecanoic acid (hereinafter to be also referred to as HYB), 10-oxo-cis-12-octadecenoic acid (hereinafter to be also referred to as KetoA) and 10-oxo-trans-11-octadecenoic acid (hereinafter to be also referred to as KetoC)) to be used in this Example were prepared according to the method of WO 2013/168310. In addition, HYA, αHYA, γHYA were prepared by reference to the report in Biochemical and Biophysical Research Communications 416 (2011) p. 188-193, and the like. The stearic acid, oleic acid, linoleic acid, ricinoleic acid, DHA and EPA to be used in this Example were purchased from Nacalai Tesque, INC. The ricinoleic acid to be used in this Example was purchased from Sigma-Aldrich Co. LLC.

Example 1 Proliferation Inhibitory Effect (In Vitro) on *Helicobacter pylori* TK1029 Strain by $ED_{50}$ Measurement

*Helicobacter pylori* TK1029 strain (clinical isolate) was cultured in *Brucella* broth containing 10% FCS and $1\times10^6$ CFU of bacteria were respectively added to 3 mL of Brain-Heart Infusion Broth (BHI) media (previously added with free fatty acid (stearic acid, oleic acid, linoleic acid, ricinoleic acid, HYA) at 0, 0.5, 5, 50, 500 µg/mL) containing 2% FCS in a 6-well plate. Shaking culture was performed under conditions of temperature 37° C., humidity 100%, microaerobic (5% $O_2$, 10% $CO_2$, 85% $N_2$), the culture medium (0.1 mL) from each well was applied to NISSUI plate, *Helicobacter* agar medium 15 hr and 25 hr later, and the number of colonies formed after microaerobic culture for 3 days was counted. This viable count is expressed as a logarithm and, on the logarithmic graph where the detection limit of viable count is $10^2$, the concentration at which the number of viable cells in the medium added with free fatty acid is half the number of viable cells in the medium not added with free fatty acid was taken as the $ED_{50}$ value, ($ED_{50}$ value is a concentration at which the viable count of the medium added with free fatty acid is {10×(viable count of the medium not added with free fatty acid)$^{1/2}$}). As a result, HYA already showed an anti-*Helicobacter pylori* effect at 15 hr after culturing as evidenced by $ED_{50}$ value about 1000-100 times lower than that of fatty acid having 18 carbon atoms and not having a hydroxyl group (stearic acid, oleic acid, linoleic acid), and showed an anti-*Helicobacter pylori* effect as evidenced by $ED_{50}$ value about 10 times lower than that of ricinoleic acid which is a fatty acid having 18 carbon atoms and a hydroxyl group (Table 1). Even at 25 hr after culturing, HYA showed an anti-*Helicobacter pylori* effect with $ED_{50}$ values remarkably lower than or the same level as those of the above-mentioned fatty acids.

TABLE 1

| fatty acid | 15 hr later (µg/mL) | 25 hr later (µg/mL) |
| --- | --- | --- |
| stearic acid | 500 | >500 |
| oleic acid | 50 | >50 |
| linoleic acid | 50 | 50 |
| ricinoleic acid | 5 | 0.5 |
| HYA | 0.5 | 0.5 |

Example 2 Proliferation Inhibitory Effect (In Vitro) of HYA on *Helicobacter pylori*

Figures 1, 2:
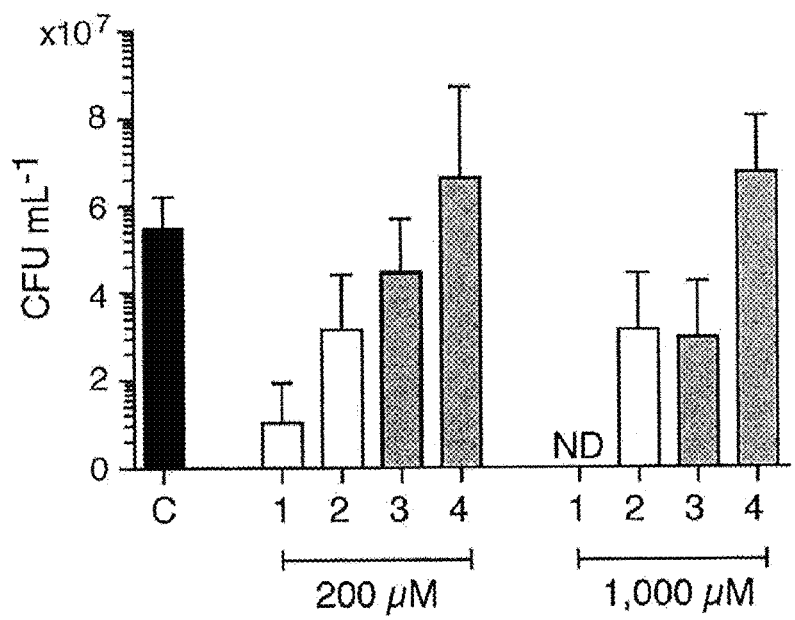

*Helicobacter pylori* SS1 strain, TN2GF4 strain, ATCC43579 strain, NCTC11637 strain, TY281 strain, TY1345 strain were each inoculated to a 6-well plate containing 3 mL of a liquid medium (*Brucella* broth added with 10% FCS), and fatty acid (200 µM or 1000 µM) and menaquinone (MK-4) 100 µg/mL were added. After static culture for 3 days at temperature 37° C., microaerobic conditions (5% 02, 10% 002, 85% $N_2$), the culture medium was applied on a *Helicobacter* agar plate, cultured for 3 days and the resulting colonies were counted (FIG. 1-1 A: SS1 strain, FIG. 1-2 B: TN2GF4 strain, FIG. 1-3 C: ATCC43579 strain, FIG. 1-4 D: NCTC11637 strain, FIG. 1-5 E: TY281 strain, FIG. 1-6 F: TY1345 strain. Item C: control (no addition), Item 1: HYA addition, Item 2: HYA and menaquinone addition, Item 3: linoleic acid addition, Item 4: linoleic acid and menaquinone addition). HYA suppressed proliferation of *Helicobacter pylori* SS1 strain, TN2GF4 strain, ATCC43579 strain, NCTC11637 strain, TY281 strain, TY1345 strain more than linoleic acid. Addition of menaquinone (MK-4) mitigated inhibition of proliferation of *Helicobacter pylori* by fatty acid.

Example 3 Proliferation Inhibitory Effect (In Vitro) of Low Concentration HYA on *Helicobacter pylori*

*Helicobacter pylori* SS1 strain, TN2GF4 strain, TK1029 strain, RC-1 strain were each inoculated to a 6-well plate containing 2 mL of a liquid medium (BHI added with 5% FCS), and fatty acid (20 µM) and menaquinone (MK-4) 100 µg/mL were added. After shaking culture for 24 hr at temperature 37° C., microaerobic conditions (5% 02, 10% $CO_2$, 85% $N_2$), the culture medium was applied on a *Helicobacter* agar plate, cultured for 3 days and the resulting colonies were counted (FIG. 2-1 A: SS1 strain, FIG. 2-2 B: TN2GF4 strain, FIG. 2-3 C: TK1029 strain, FIG. 2-4 D: RC-1 strain. Item 1: control (menaquinone no addition), Item 2: control (menaquinone 100 µg/mL addition), Item 3: HYA 20 µM (menaquinone no addition), Item 4: HYA 20 µM (menaquinone 100 µg/mL addition), Item 5: linoleic acid 20 µM (menaquinone no addition), Item 6: linoleic acid 20 µM (menaquinone 100 µg/mL addition). *, P<0.0001 vs. Control (ordinary one-way ANOVA)). HYA suppressed proliferation of *Helicobacter pylori* SS1 strain, TN2GF4 strain, TK1029 strain, RC-1 strain more than linoleic acid. Addition of menaquinone (MK-4) mitigated inhibition of proliferation of *Helicobacter pylori* by fatty acid.

Example 4 *Helicobacter pylori* SS1 Strain and TN2GF4 Strain Inhibitory Effect (In Vivo) of Fatty Acid A 5-week-old C57BL/6 female mouse was orally infected 3 times with *Helicobacter pylori* SS1 strain or TN2GF4 strain (1-5×10$^8$ CFU) every other day and dissected at 2 weeks from the final infection day, and the number of bacteria in the gastric mucosa was counted. The measurement and the number of bacteria in the gastric mucosa was performed as follows. First, the greater curvature of the stomach of the mouse was incised with scissors for ophthalmology, and the contents were washed away with phosphate buffered saline (pH 7.4, PBS). Next, the mucous membrane was scraped with a slide glass, 1 mL of PBS was added, the mixture was sandwiched between ground glass parts of two glass slides and evenly crushed to prepare a gastric mucosa suspension. The culture medium was applied on a *Helicobacter* agar plate, cultured for 3 days and the resulting colonies were counted. Water added with fatty acid (200 µM) (HYA, HYB, KetoA, KetoC, linoleic acid, oleic acid, DHA, EPA) was given to the mice from 1 week before infection. The control was free of fatty acid addition (FIG. 3-1 A: infected with SS1 strain, FIG. 3-2 B: infected with TN2GF4 strain). HYA significantly suppressed the number of *Helicobacter pylori* in both SS1 strain and TN2GF4 strain, as compared to the control, and showed a strong suppressive action as compared to HYB, KetoA, KetoC, linoleic acid, oleic acid, DHA and EPA.

Figures 1, 2, 3:
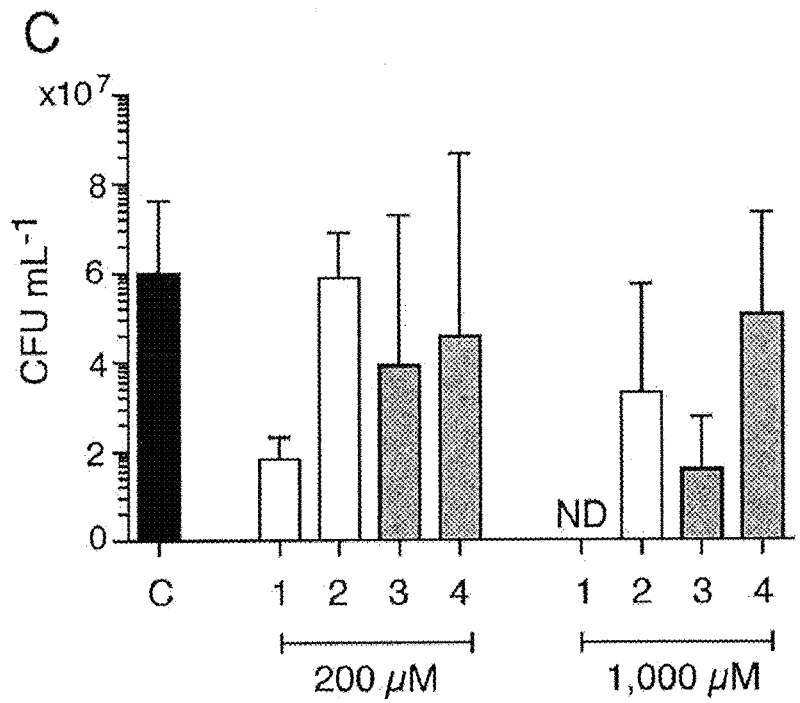
Figures 1, 2, 3, 4:
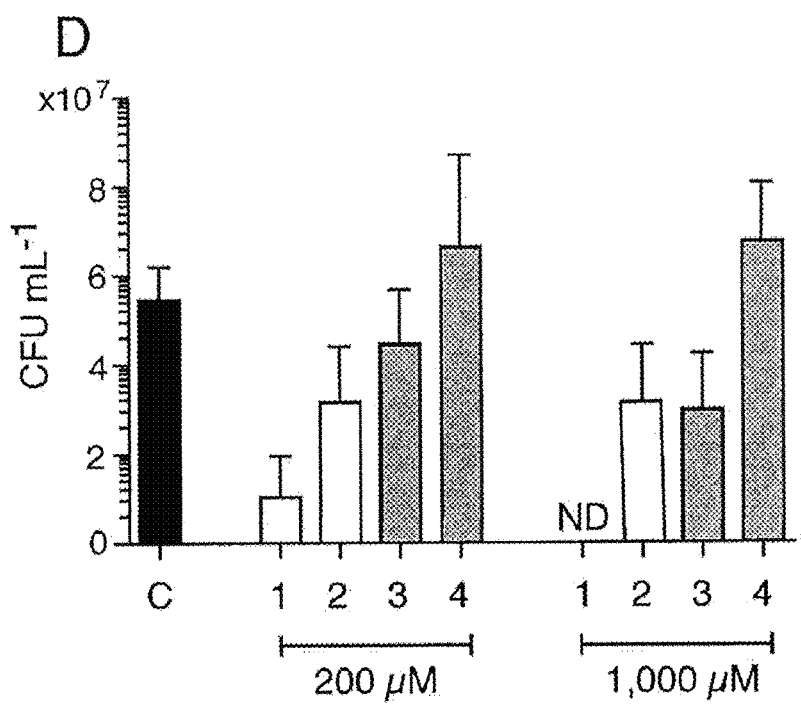
Figures 1, 2, 3, 4, 5:
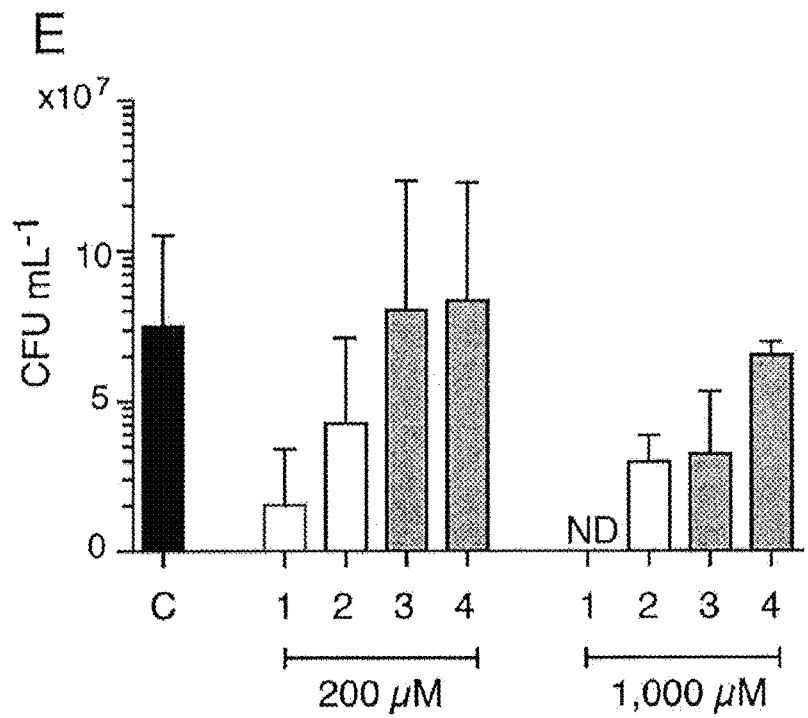
Figures 1, 2, 3, 4, 5, 6:
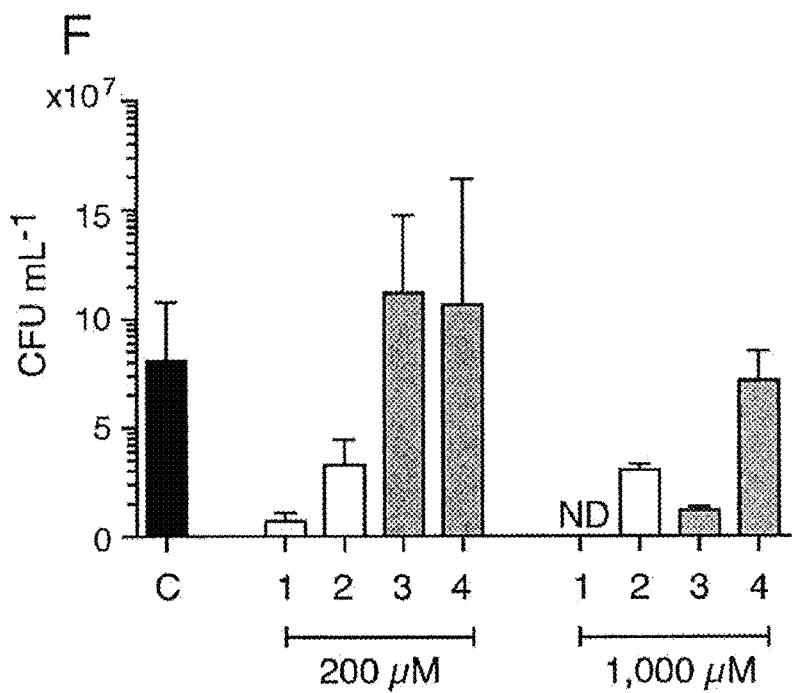
Figures 1, 2:
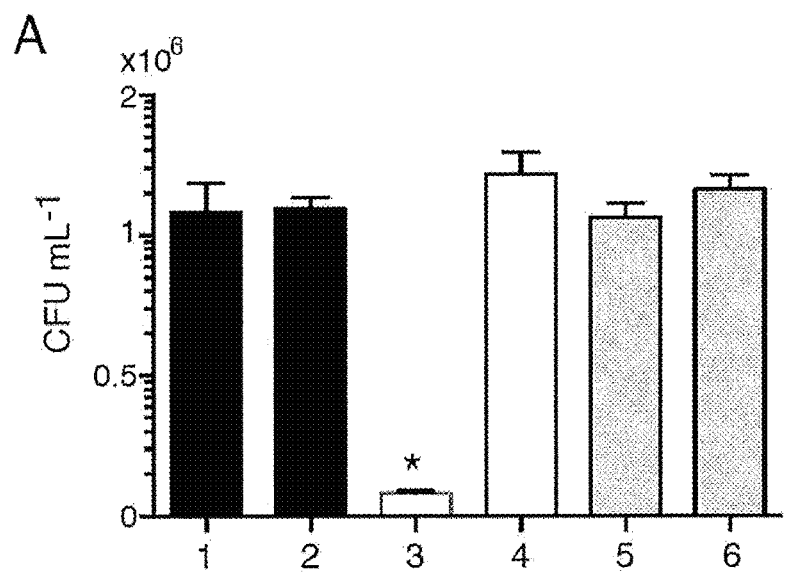
Figure 2:
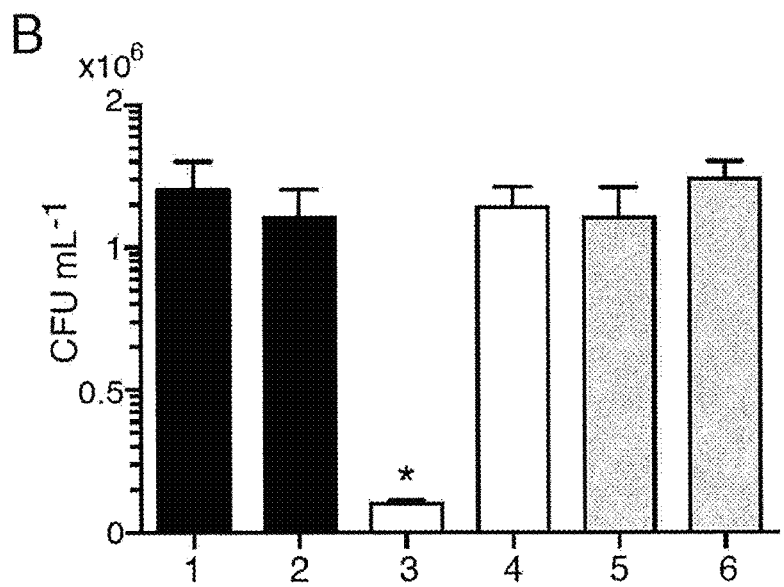
Figures 2, 3:
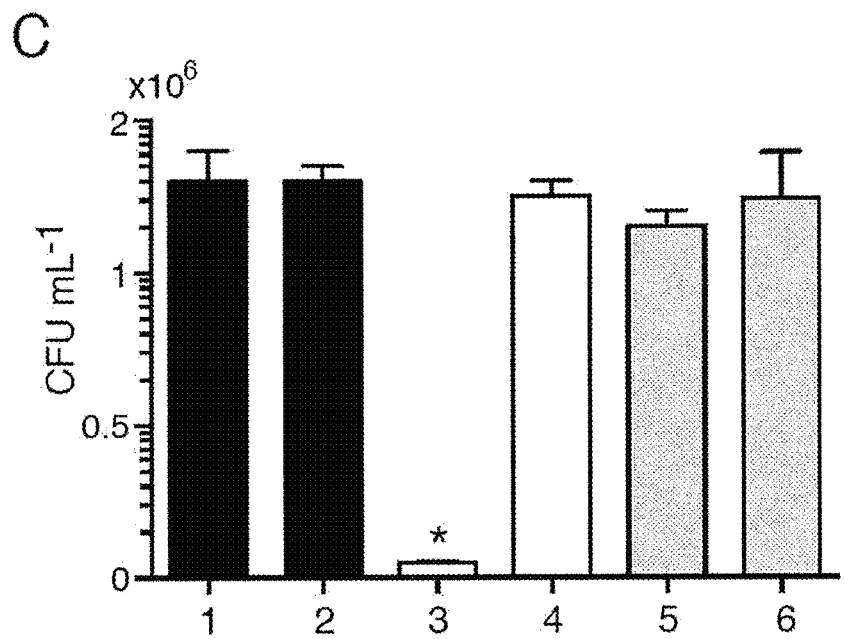
Figures 2, 3, 4:
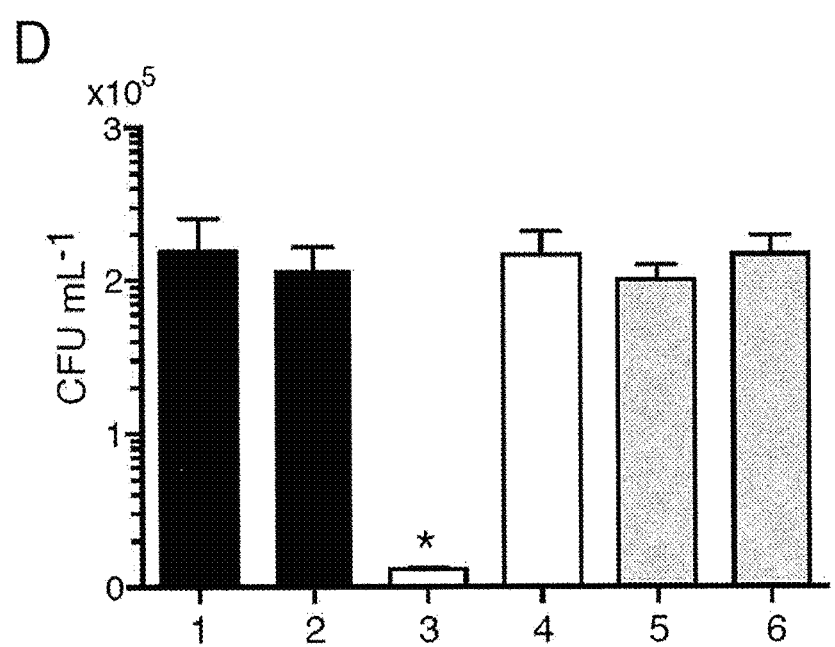
Figures 1, 3:
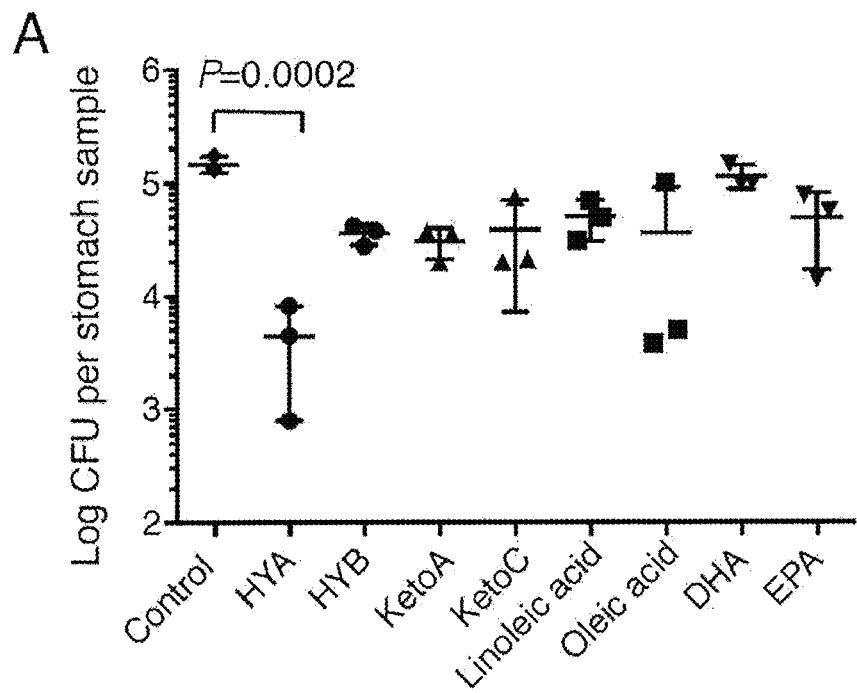
Figures 2, 3:
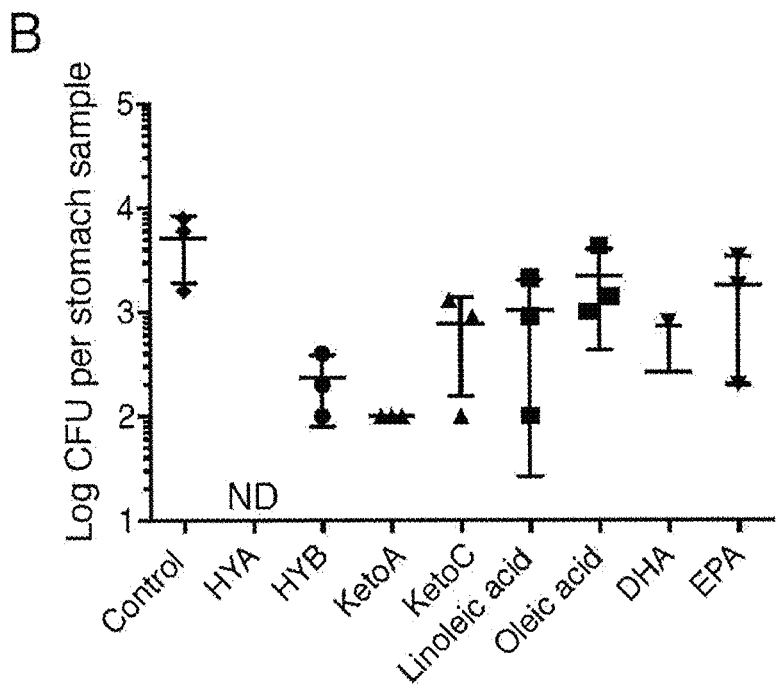
Figures 1, 4:
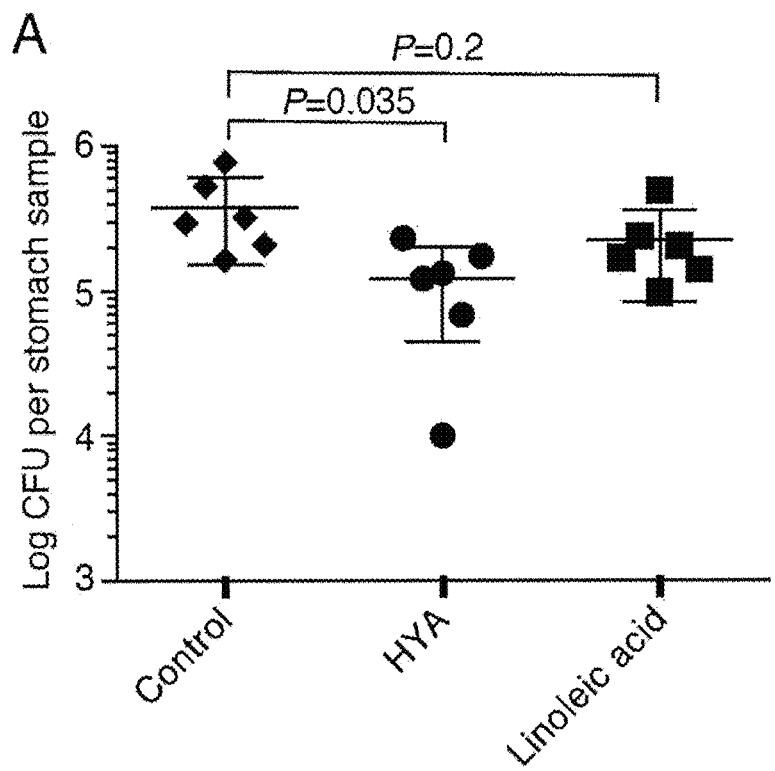
Figures 2, 4:
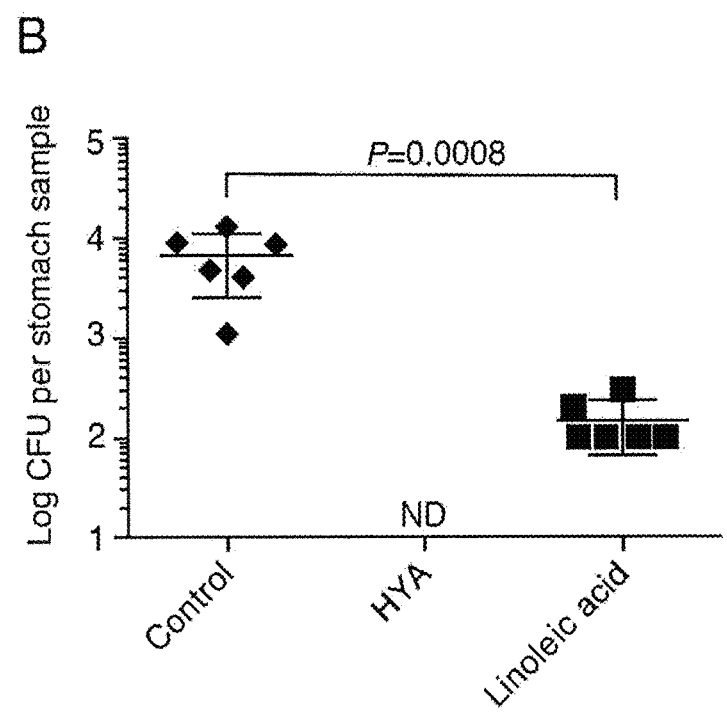
Figures 3, 4:
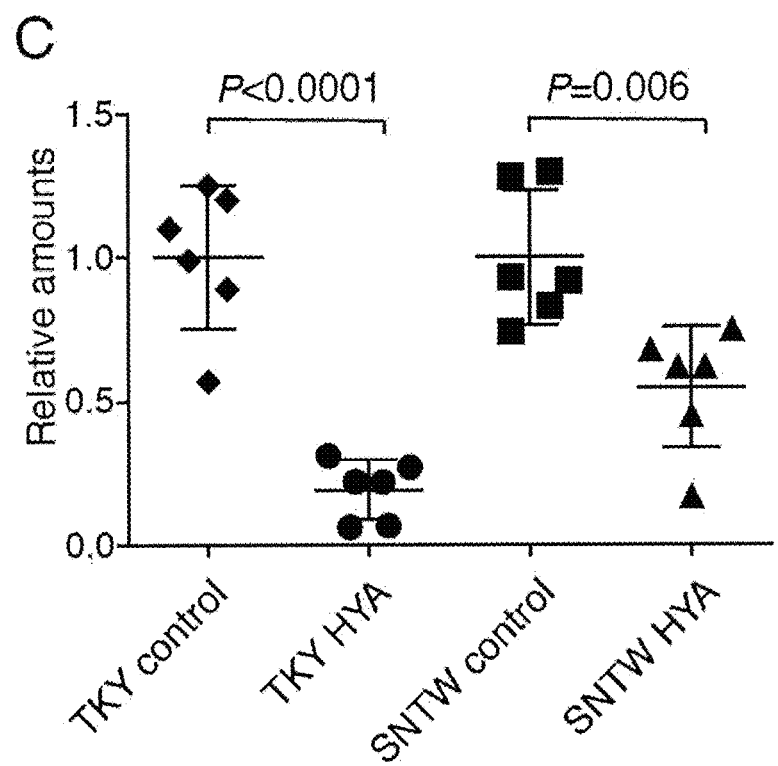
Figures 1, 5:
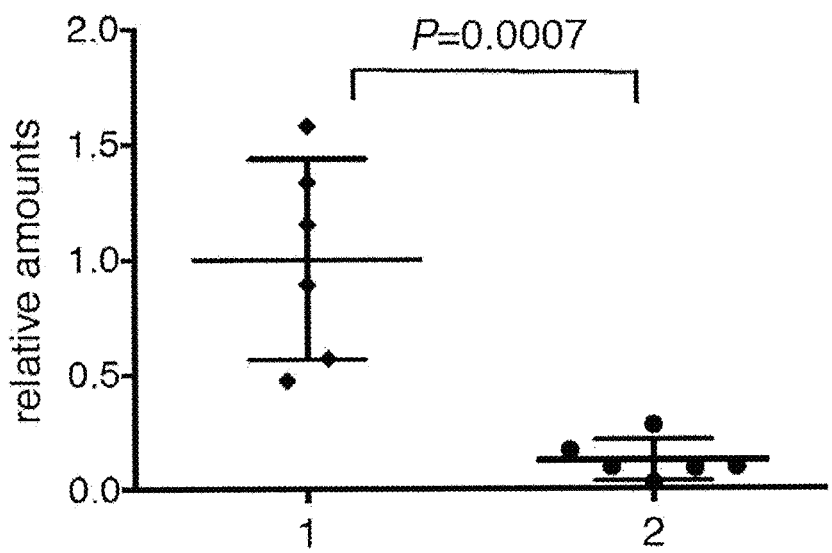
Figures 2, 5:
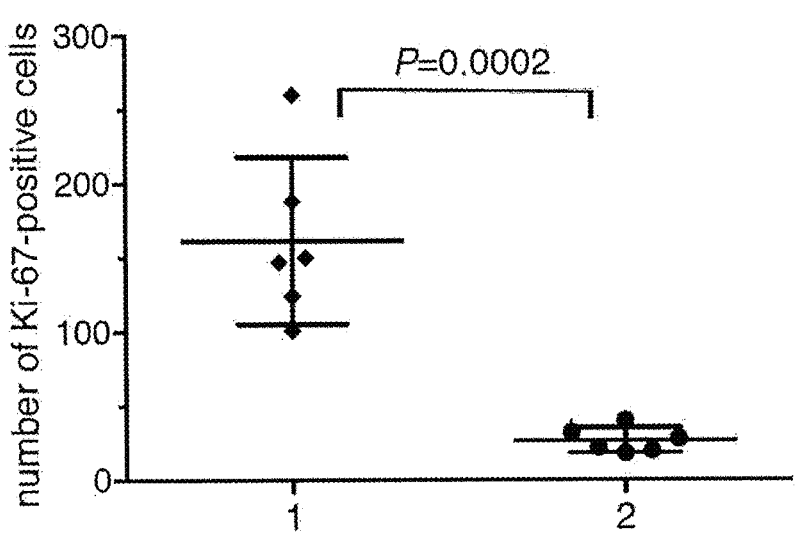
Figures 3, 5:
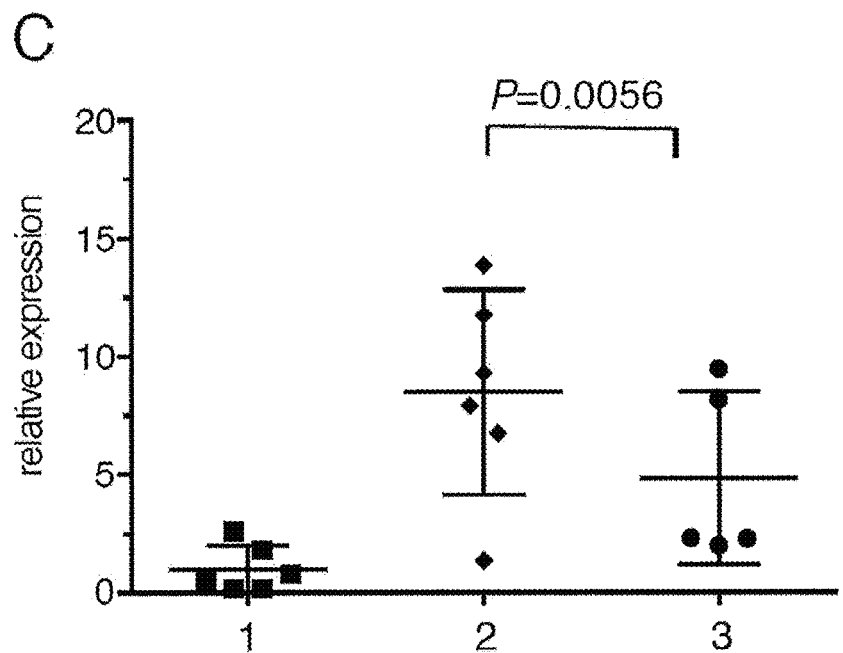
Figures 4, 5:
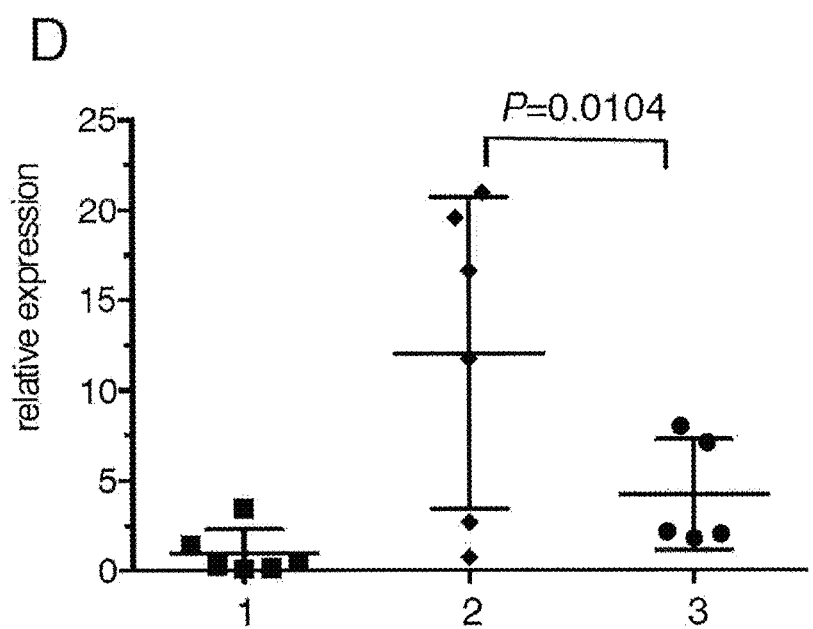
Figures 1, 6:
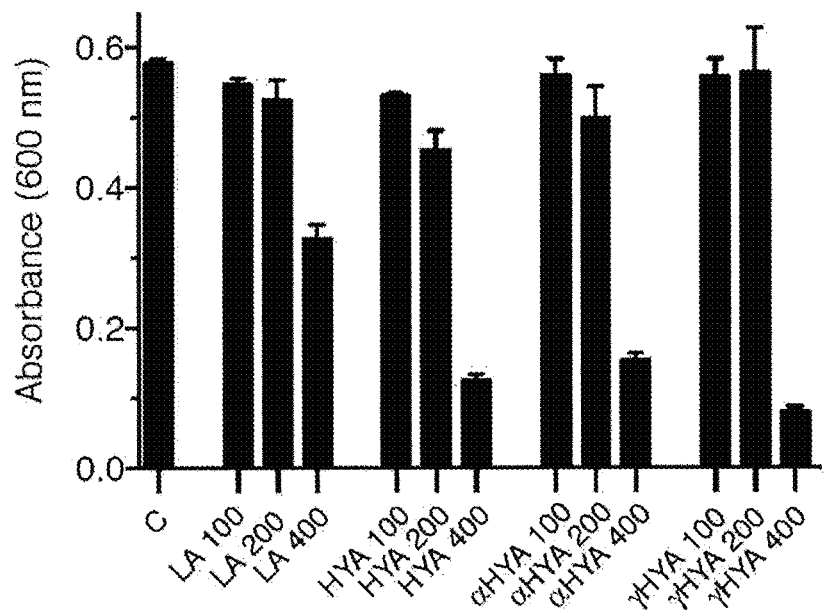
Figures 2, 6:
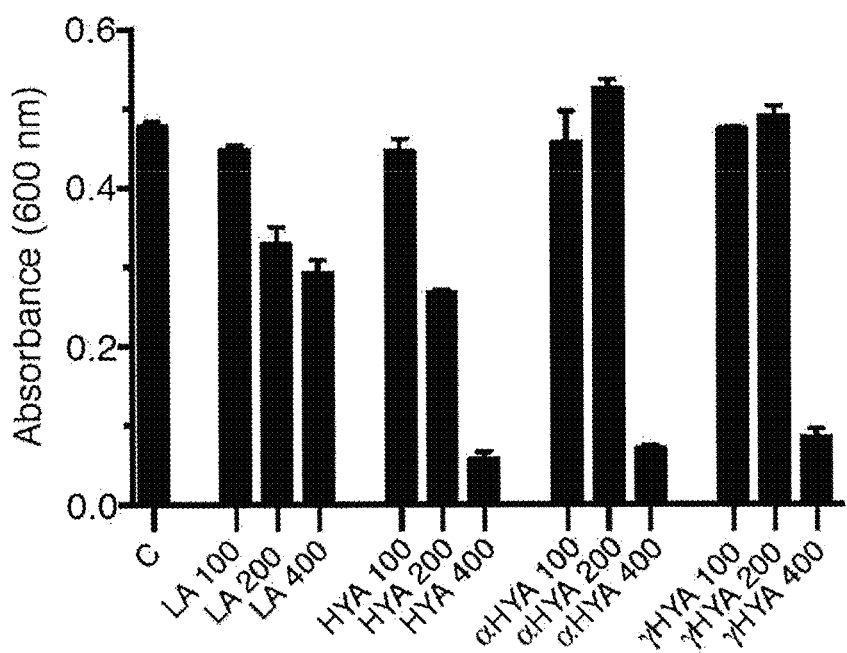
Figures 3, 6:
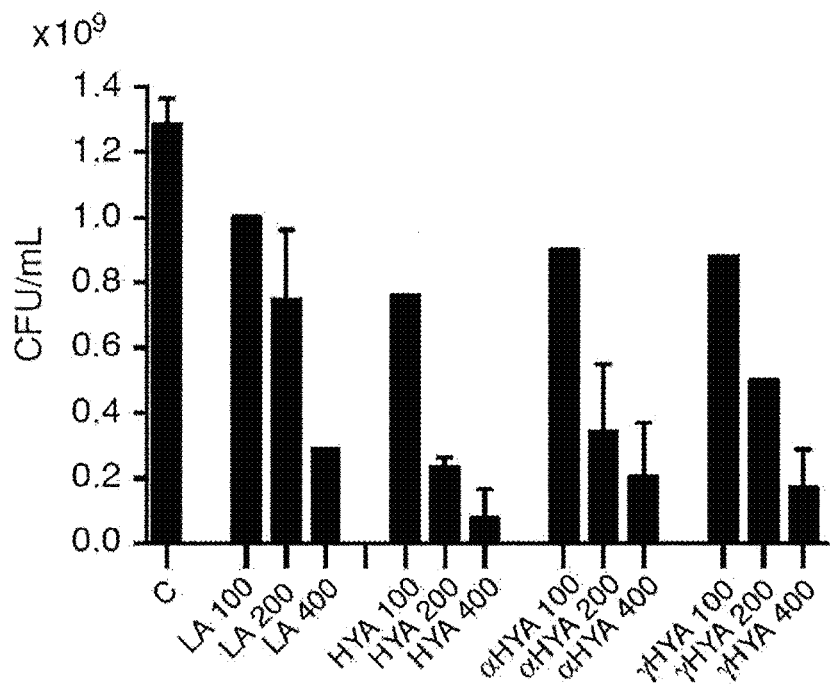
Figures 4, 6:
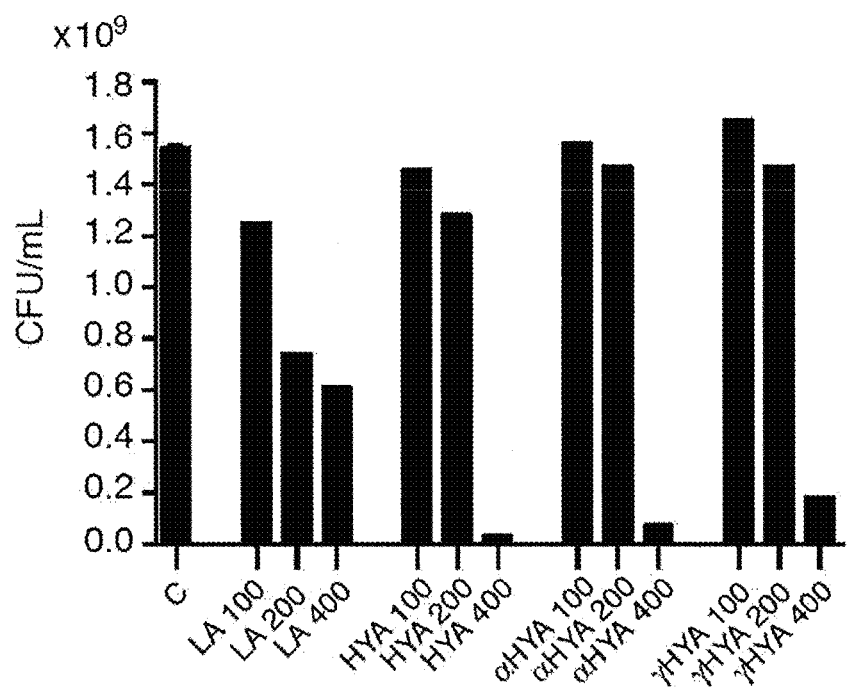

Example 5 Proliferation Inhibitory Effect (In Vivo) of HYA on *Helicobacter* Bacteria A 5-week-old C57BL/6 female mouse was orally infected 3 times with *Helicobacter pylori* SS1 strain or TN2GF4 strain (1-5×10$^8$ CFU) every other day and dissected at 2 weeks from the final infection day, and the number of bacteria in the gastric mucosa was counted. Water added with HYA or linoleic acid (200 µM) was given to the mice from 1 week before infection (FIG. 4-1 A: SS1 strain, FIG. 4-2 B: TN2GF4 strain). A 5-week-old C57BL/6 female mouse was orally infected only once with a stomach suspension of *Helicobacter suis* TKY strain or SNTW101 strain-infected mouse and dissected 2 weeks later, and the number of bacteria in the gastric mucosa was counted. Water added with HYA (200 µM) was given to the mouse from one week before the infection (FIG. 4-3 C). As a result, HYA inhibited proliferation of the *Helicobacter pylori* SS1 strain, *Helicobacter pylori* TN2GF4 strain, *Helicobacter suis* TKY strain, *Helicobacter suis* SNTW101 strain. The measurement of the number of *Helicobacter suis* bacteria in the stomach of the infected mouse was performed as follows.

DNA was prepared from a part of the stomach tissue by using DNeasy Blood & Tissue Kit (Qiagen) and real-time PCR (model: CFX96 (Bio-Rad)) was performed. As the primer for *Helicobacter suis* quantification, the following was used by reference to Diagn. Microbiol. Infect. Dis. 46(1):1-7, 2003. HeilF (5' AAG TCG AAC GAT GAA GCC TA 3') (SEQ ID NO: 1) HeilR (5' ATT TGG TAT TAA TCA CCA TTT C 3') (SEQ ID NO: 2)

The following were used as the primers for β-actin quantification of the mouse by reference to J. Clin. Microbiol. 37:1958-1963, 1999.

```
                                        (SEQ ID NO: 3)
     5' TCACCCACACTGTGCCCATCTACGA 3'

(SEQ ID NO: 4)
     5' GGATGCCACAGGATTCCATACCCA 3'
```

For quantification by real-time PCR, iQ™ SYBR Green Supermix was used. The reaction conditions were as follows.
1 cycle
  95° C. 2 min
40 cycles
  95° C. 5 sec
  55° C. 15 sec
  72° C. 45 sec Thereafter, the temperature was increased by 0.5° C. every seconds from 65° C. to 95° C. and the fluorescence was measured. Relative quantification was performed by multiplex reactions (same tube) and comparative ΔΔCT method (ABI Prism 7700) by converting to numerical values by the heilmannii-suis gene quantitative ratio per β-actin gene amount and further adjusting to make the mean of the untreated to 1.

Example 6 Pathology Onset Suppressive Effect (In Vivo) of HYA on Gastric MALT Lymphoma

*Helicobacter suis* is suspected to be the cause of the onset of gastric MALT lymphoma. A 5-week-old C57BL/6 female mouse was orally infected only once with a stomach suspension of *Helicobacter suis* TKY strain-infected mouse and dissected 6 months after the infection, and the number of bacteria in the gastric mucosa was counted according to the method described in Example 5. Water added with HYA (200 μM) was given to the mouse from one week before the infection.

(1) Measurement of the Number of *Helicobacter suis* Bacteria in the Stomach of Infected Mouse The measurement of the number of *Helicobacter suis* bacteria in the stomach of the infected mouse was performed in the same manner as in Example 5. The relative value of the number of bacteria in gastric mucosa when that with HYA non-administration is 1 is shown (FIG. 5-1 A, Item 1: HYA non-administration group, Item 2: HYA administration group). The number of bacteria was significantly suppressed in the HYA administration group compared to the non-administration group.

(2) Histochemical Analysis

Ki-67 is known as a marker for cell proliferation and cell cycle. Proliferated cells in a tumor tissue were detected by immunostaining with anti-Ki-67 antibody. A part of the stomach was fixed with 10% neutral formalin buffer to prepare a paraffin block, serial sections were cut out using a microtome and Hematoxylin Eosin (HE) staining was performed. Ki-67 (Clone SP6) rabbit monoclonal antibody (Thermo Fisher Scientific Inc.) diluted 1:300 was used as a dilution antibody, Histofine Simple Stain mouse MAX-PO® (NICHIREI BIOSCIENCES INC., Code: 414341) DAB staining (DAKO Inc.) was used as a secondary antibody, and Hematoxylin was used for comparison staining. As the negative control, rabbit IgG antibody (Code No. X 0936 Lot 050 (DAKO Inc.)) was used. The number of Ki-67 positive cells in lymphoid follicle when that with HYA non-administration is 1 is shown (FIG. 5-2 B, Item 1: HYA non-administration group, Item 2: HYA administration group). An increase in the number of Ki-67 positive cells was significantly suppressed in the HYA administration group compared to the non-administration group.

(3) Quantification of CD19, CD20 Expressions

CD19 and CD20 are cell surface markers for B-cell lymphoma. Using real-time reverse transcription PCR (real-time RT-PCR), the expression levels of CD19 and CD20 were measured. Using NucleoSpin (registered trade mark) RNA Kit (Takara Bio Inc.), RNA was prepared from mouse gastric mucosa. Using PrimeScript™ RT Reagent Kit (Takara Bio Inc.), cDNA was prepared from RNA. For real-time RT-PCR, KAPA SYBR Fast ROX Low qPCR kit (KAPA BIOSYSTEMS Inc.) and QuantStudio7 Flex Real-time PCR System (Thermo Fisher Scientific Inc.) were used.

The following were used as the primers for quantification of CD19 expression.

```
                                        (SEQ ID NO: 5)
     Fw: 5'-AGTGACTAGCCTGGACTT-3'

(SEQ ID NO: 6)
     Rv: 5'-ACTGACTGACACCATCTG-3'
```

The following were used as the primers for quantification of CD20 expression.

```
                                        (SEQ ID NO: 7)
     Fw: 5'-CAGGAAGAGTTTGGTCAA-3'

(SEQ ID NO: 8)
     Rv: 5'-GGTTCACAGTCGTAGATAT-3'
```

The following were used as the primers for quantification of glyceraldehyde-3-phosphate (GAPDH) expression.

```
                                        (SEQ ID NO: 9)
     Fw: 5'-TGTGTCCGTCGTGGATCTGA-3'

(SEQ ID NO: 10)
     Rv: 5'-TTGCTGTTGAAGTCGCAGGAG-3'
```

The conditions of 2-step real-time RT-PCR were as follows.
1 cycle
  95° C. 3 min
40 cycles
  95° C. 3 sec
  60° C. 20 sec The expression level of CD19 or CD20 relative to that of glyceraldehyde-3-phosphate dehydrogenase (GAPDH) was converted to a numerical value and the value was further adjusted to make the average expression of CD19 or CD20 of the non-infection group 1. The CD20 relative expression levels in the HYA administration group and non-administration group are shown (FIG. 5-3 C, Item 1: non-infection group, Item 2: HYA non-administration group, Item 3: HYA administration group). Similarly, the CD19 relative expression levels in the HYA administration group and non-administration group are shown (FIG. 5-4 D, Item 1: non-infection group, Item 2: HYA non-administration group, Item 3: HYA administration group). As a result, the relative expression level was significantly suppressed in the HYA administration group compared to the non-administration group.

Example 7 Proliferation Inhibitory Effect (In Vitro) of HYA on *Campylobacter jejuni* ATCC33560 Strain and *Campylobacter coli* ATCC33559 Strain

*Campylobacter jejuni* ATCC33560 strain or *Campylobacter coli* ATCC33559 strain preserved at −80° C. was applied on a CODA agar medium added with SR0155E and cultured for 2 days in an incubator (5% $O_2$, 10% $CO_2$, 85% $N_2$, humidity 100%, 42° C.). The resulting colonies were picked up, inoculated to 10% FBS-added *Brucella* liquid medium and shaken in the incubator overnight. 2 mL of 5% FBS-added *Brucella* liquid medium containing *Campylobacter jejuni* ATCC33560 strain or *Campylobacter coli* ATCC33559 strain at a concentration of $1\times10^6$ CFU/mL was dispensed to each well of a 12-well plate, fatty acid was added at an optional concentration (0, 100, 200, 400 μM), and the mixture was shaken in the incubator for 24 hr. After 24 hr, the absorbance (600 nm) of the liquid medium after shaking was measured. On the other hand, the liquid medium at 24 hr after shaking was diluted $1\times10^6$-fold with BSG (PBS containing 0.01% gelatin, pH 7.4), 0.1 mL was applied on 10% FBS-added *Brucella* agar medium, cultured in the incubator for 2 days and the number of the resulting colonies was measured (FIGS. 6-1 to 6-4, C: control, LA 100: linoleic acid 100 μM, LA 200: linoleic acid 200 μM, LA 400: linoleic acid 400 μM, HYA 100: HYA 100 μM, HYA 200: HYA 200 μM, HYA 400: HYA 400 μM, αHYA 100: αHYA 100 μM, αHYA 200: αHYA 200 μM, αHYA 400: αHYA 400 μM, γHYA 100: γHYA 100 μM, γHYA 200: γHYA 200 μM, γHYA 400: γHYA 400 μM). As a result, HYA, αHYA, γHYA inhibited proliferation of *Campylobacter jejuni* ATCC33560 strain or *Campylobacter coli* ATCC33559 strain in a concentration dependent manner, and showed a strong inhibitory action compared to linoleic acid.

From the above results, it was shown that a fatty acid having 18 carbon atoms and a hydroxyl group at the 10-position has an inhibitory action on the proliferation of a bacterium provided with a menaquinone synthesis route via futalosine or a futalosine derivative such as *Helicobacter pylori, Helicobacter suis* and the like, a suppressive action on an increase in the number of Ki-67 positive cells, a suppressive action on an increase in the CD19 expression level and CD20 expression level, and a suppressive action on the onset of pathology of gastric MALT lymphoma. In addition, it was shown that a fatty acid having 18 carbon atoms and a hydroxyl group at the 10-position has an inhibitory action on proliferation of *Campylobacter jejuni* and *Campylobacter* coll.

INDUSTRIAL APPLICABILITY

In the present invention, it was found that a fatty acid having 18 carbon atoms and a hydroxyl group at the 10-position inhibits proliferation of a bacterium provided with a menaquinone synthesis route via futalosine or a futalosine derivative. The composition containing the fatty acid can be used in various fields such as pharmaceutical product, food, feed and the like, and is industrially extremely useful.

This application is based on a patent application No. 2017-053056 filed in Japan (filing date: Mar. 17, 2017), the contents of which are incorporated in full herein.

The invention claimed is:

1. A method for preventing development of a disease selected from the group consisting of acute gastritis, chronic gastritis, nodular gastritis, stomach cancer, stomach MALT lymphoma, diffuse large B-cell lymphoma, idiopathic thrombocytopenia purpura, chronic urticaria, and Parkinson's disease in a patient infected with *Helicobacter pylori* or *Helicobacter suis* comprising administering a fatty acid having 18 carbon atoms and a hydroxyl group at the 10-position to a subject.

2. A method for preventing development of food poisoning in a subject infected with *Campylobacter jejuni* or *Campylobacter coli* comprising administering a fatty acid having 18 carbon atoms and a hydroxyl group at the 10-position to the subject.

3. The method according to claim 1, wherein the fatty acid has a cis double bond at at least the 12-position.

4. The method according to claim 3, wherein the fatty acid is at least one selected from the group consisting of 10-hydroxy-cis-12-octadecenoic acid, 10-hydroxy-cis-12,cis-15-octadecadienoic acid and 10-hydroxy-cis-6,cis-12-octadecadienoic acid.

5. The method according to claim 4, wherein the fatty acid is 10-hydroxy-cis-12-octadecenoic acid.

6. The method according to claim 2, wherein the fatty acid has a cis double bond at at least the 12-position.

7. The method according to claim 6, wherein the fatty acid is at least one selected from the group consisting of 10-hydroxy-cis-12-octadecenoic acid, 10-hydroxy-cis-12,cis-15-octadecadienoic acid and 10-hydroxy-cis-6,cis-12-octadecadienoic acid.

8. The method according to claim 7, wherein the fatty acid is 10-hydroxy-cis-12-octadecenoic acid.

9. A method for preventing Guillain-Barre syndrome in a patient infected with *Campylobacter jejuni* or *Campylobacter coli* comprising administering a fatty acid having 18 carbon atoms and a hydroxyl group at the 10-position to a subject.

* * * * *

SEQUENCE LISTING

```
<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
aagtcgaacg atgaagccta                                             20

<210> SEQ ID NO 2
<211> LENGTH: 22
<212> TYPE: DNA
<213> ORGANISM: Artificial Sequence
<220> FEATURE:
<223> OTHER INFORMATION: primer

<400> SEQUENCE: 2
atttggtatt aatcaccatt tc                                          22

<210> SEQ ID NO 3
<211> LENGTH: 25
<212> TYPE: DNA
<213> ORGANISM: Artificial Sequence
<220> FEATURE:
<223> OTHER INFORMATION: primer

<400> SEQUENCE: 3
tcacccacac tgtgcccatc tacga                                       25
```

```
<210> SEQ ID NO 4
<211> LENGTH: 24
<212> TYPE: DNA
<213> ORGANISM: Artificial Sequence
<220> FEATURE:
<223> OTHER INFORMATION: primer

<400> SEQUENCE: 4
ggatgccaca ggattccata ccca                                          24

<210> SEQ ID NO 5
<211> LENGTH: 18
<212> TYPE: DNA
<213> ORGANISM: Artificial Sequence
<220> FEATURE:
<223> OTHER INFORMATION: primer

<400> SEQUENCE: 5
agtgactagc ctggactt                                                 18

<210> SEQ ID NO 6
<211> LENGTH: 18
<212> TYPE: DNA
<213> ORGANISM: Artificial Sequence
<220> FEATURE:
<223> OTHER INFORMATION: primer

<400> SEQUENCE: 6
actgactgac accatctg                                                 18

<210> SEQ ID NO 7
<211> LENGTH: 18
<212> TYPE: DNA
<213> ORGANISM: Artificial Sequence
<220> FEATURE:
<223> OTHER INFORMATION: primer

<400> SEQUENCE: 7
caggaagagt ttggtcaa                                                 18

<210> SEQ ID NO 8
<211> LENGTH: 19
<212> TYPE: DNA
<213> ORGANISM: Artificial Sequence
<220> FEATURE:
<223> OTHER INFORMATION: primer

<400> SEQUENCE: 8
ggttcacagt cgtagatat                                                19

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
tgtgtccgtc gtggatctga                                               20

<210> SEQ ID NO 10
<211> LENGTH: 21
<212> TYPE: DNA
<213> ORGANISM: Artificial Sequence
<220> FEATURE:
```

-continued

```
<223> OTHER INFORMATION: primer

<400> SEQUENCE: 10
ttgctgttga agtcgcagga g                                                    21
```